United States Patent
Yamane et al.

(10) Patent No.: US 9,643,949 B2
(45) Date of Patent: May 9, 2017

(54) METHOD FOR PRODUCING GLYCOLIDE

(71) Applicant: Kureha Corporation, Tokyo (JP)

(72) Inventors: Kazuyuki Yamane, Tokyo (JP); Yoshiko Ikeyama, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 0 days.

(21) Appl. No.: 14/770,900

(22) PCT Filed: Mar. 18, 2014

(86) PCT No.: PCT/JP2014/057257
§ 371 (c)(1),
(2) Date: Aug. 27, 2015

(87) PCT Pub. No.: WO2014/156809
PCT Pub. Date: Oct. 2, 2014

(65) Prior Publication Data
US 2016/0002197 A1    Jan. 7, 2016

(30) Foreign Application Priority Data

Mar. 27, 2013    (JP) .................................. 2013-066000

(51) Int. Cl.
*C07D 319/12*    (2006.01)
(52) U.S. Cl.
CPC .................................. *C07D 319/12* (2013.01)
(58) Field of Classification Search
None
See application file for complete search history.

(56) References Cited

U.S. PATENT DOCUMENTS

| | | |
|---|---|---|
| 2,668,162 A | 2/1954 | Lowe |
| 4,835,293 A | 5/1989 | Bhatia |
| 5,023,349 A | 6/1991 | Bhatia |
| 5,830,991 A | 11/1998 | Shiiki et al. |
| 2003/0191326 A1 | 10/2003 | Yamane et al. |
| 2010/0168446 A1 | 7/2010 | Yamane et al. |

FOREIGN PATENT DOCUMENTS

| | | |
|---|---|---|
| CN | 1446209 A | 10/2003 |
| EP | 1 310 496 A1 | 5/2003 |
| FR | 2692263 A1 | 12/1993 |
| JP | H09328481 A | 12/1997 |
| JP | 2000119269 A | 4/2000 |
| KR | 2003-0040371 A | 5/2003 |
| WO | WO0214303 A1 | 2/2002 |
| WO | WO2008102607 A1 | 8/2008 |

OTHER PUBLICATIONS

English translation of International Preliminary Report on Patentability and Written Opinion mailed Oct. 8, 2015, in PCT International Application No. PCT/JP2014/057257.
International Search Report of PCT/JP2014/057257 sent on Apr. 22, 2014.
Notification of First Office Action issued May 11, 2016, in Chinese Patent Application No. 201480007879.0, with English translation.
Notification of Reason for Refusal issued Sep. 22, 2016, in Korean Patent Application No. 10-2015-7021535, with English translation.
Extended European Search Report issued Jul. 22, 2016, in European Patent Application No. 14775593.8.
Chinese Office Action, dated Feb. 4, 2017, for Chinese Application No. 201480007879.0, along with an English translation.

*Primary Examiner* — Golam M M Shameem
*Assistant Examiner* — Laura Daniel
(74) *Attorney, Agent, or Firm* — Birch, Stewart, Kolasch & Birch, LLP

(57) ABSTRACT

A method for producing a GL comprising: (I) a heating step of heating a mixture either under normal pressure or reduced pressure at a temperature at which a polyglycolic acid (PGA) undergoes depolymerization, the mixture containing the PGA and a polyethylene glycol ether which is represented by the formula: X—O—(—CH$_2$CH$_2$—O—)$_p$—Y (wherein X and Y are each independently an alkyl group or an aryl group having from 2 to 20 carbon atoms, and p is an integer from 1 to 5) and which has a molecular weight of from 150 to 450 and a boiling point of from 130 to 220° C. at a pressure of 3 kPa; (II) a solution-forming step in which the mixture is rendered in a solution state in which a melt phase of the PGA and a liquid phase consisting of the polyethylene glycol ether essentially form a uniform phase; (III) a GL production step in which a glycolide (GL) is produced by a depolymerization reaction of the PGA by continuing to heat the mixture in the solution state; (IV) a distillation step of distilling off the produced GL together with the polyethylene glycol ether (B) from the depolymerization reaction system; and (V) a recovery step of recovering the GL from the distillate.

20 Claims, No Drawings

METHOD FOR PRODUCING GLYCOLIDE

TECHNICAL FIELD

The present invention relates to a method for producing a glycolide efficiently and economically by means of the depolymerization of a polyglycolic acid.

The glycolide obtained by the production method of the present invention is useful as a monomer for ring-opening polymerization. More specifically, the glycolide obtained by the production method of the present invention may be subjected to ring-opening polymerization alone or may be copolymerized with other comonomers to obtain polyglycolide (that is, polyglycolic acid) or various copolymers. Polyglycolic acid (copolymer) is useful as a biodegradable polymeric material, a polymeric material for medical use, and the like.

Further, the method for producing a glycolide of the present invention is useful not only as a method for producing a glycolide via a polyglycolic acid with a low molecular weight such as a glycolic acid oligomer, but also as a method for recycling product waste or mold wastes of a polyglycolic acid with a high molecular weight by converting the substance into a glycolide of a monomer.

BACKGROUND ART

Aliphatic polyesters such as polyglycolic acid or polylactic acid are hydrolyzed in vivo and, in natural environments, are metabolized and degraded to water and carbon dioxide by microorganisms. Therefore, aliphatic polyesters have attracted attention as biodegradable polymeric materials which can be substituted for medical materials or commodity resins. Of these aliphatic polyesters, polyglycolic acid has not only high biodegradability and hydrolyzability when an alkaline solution or the like, for example, is used, but also excellent mechanical characteristics such as heat resistance and tensile strength and, in particular, excellent gas barrier properties when used as a film or a sheet. Therefore, polyglycolic acid is expected to be used as agricultural materials, various packaging (container) materials, or polymeric materials for medical use, and applications have been expanded by using polyglycolic acid alone or combining polyglycolic acid with other resin materials or the like.

A polyglycolic acid can be obtained by polycondensing glycolic acid, but with this method, it is difficult to obtain a polyglycolic acid with a high molecular weight. Therefore, polyglycolic acids with a high molecular weight used as molding materials or the like are often synthesized by performing ring-opening (co)polymerization on a glycolide as a cyclic ester.

That is, a polyglycolic acid can be synthesized by dehydrating and condensing glycolic acid as a monomer. However, with a polycondensation method using glycolic acid as a starting raw material, it is difficult to obtain a polyglycolic acid with a high molecular weight. Therefore, a polyglycolic acid with a high molecular weight is synthesized by performing ring-opening polymerization on a glycolide having the structure of a bimolecular cyclic ester of glycolic acid (also called a "dimeric cyclic ester" hereafter) (that is, 1,4-dioxane-2,5-dione).

In order to mass-produce a polyglycolic acid on an industrial scale using a glycolide as a starting raw material, it is indispensable to efficiently and economically supply high-purity glycolide. However, it was difficult to synthesize glycolide efficiently and economically. Glycolide is a dimeric cyclic ester with a structure in which two molecules of water are eliminated from two molecules of glycolic acid, but when glycolic acids are simply esterified with one another, a low-molecular-weight substance such as an oligomer is ordinarily formed, and it is not possible to obtain a glycolide as a dimeric cyclic ester. Therefore, a method of producing a dimeric glycolide by synthesizing a glycolic acid oligomer and then depolymerizing the oligomer, for example, has been used.

The following is an example of a method conventionally known as a technique for obtaining a dimeric cyclic ester of -hydroxycarboxylic acid such as glycolide.

U.S. Pat. No. 2,668,162 (Patent Document 1) discloses a method of pulverizing a glycolic acid oligomer into a powder form, depolymerizing the ground product by heating to 270 to 285° C. in an ultra-vacuum of from 12 to 15 torr (1.6 to 2.0 kPa) while supplying the powder into a reactor at a ratio of very small increments of approximately 20 g/hour, and then capturing a vapor containing the produced glycolide in a trap. This method can be implemented on a small scale, but it is difficult to increase the scale, and the method is not suitable for mass production. Moreover, with this method, the oligomer becomes heavy at the time of heating and remains inside the reactor as a large residue, so the yield is low and the residue cleaning operation is complex. Further, with this method, a glycolide with a high melting point is deposited on the inside wall of the recovery line together with by-products, which may plug the line, and the recovery of the deposits in the line is also difficult.

U.S. Pat. No. 4,835,293 (Patent Document 2) and U.S. Pat. No. 5,023,349 (Patent Document 3) disclose a method of heating an -hydroxycarboxylic acid oligomer to form a melt, blowing an inert gas such as nitrogen gas onto the surface of the melt, making the cyclic ester that is produced and volatilized from the surface accompany the gas flow, and then recovering the product. With this method, the production rate of the cyclic ester is small, and since a large amount of an inert gas is blown onto the melt, the production cost becomes high due to the need to preliminarily heat the inert gas. Further, with this method, an increase in weight progresses in the oligomer melt during heating, and a large amount of heavy material remains inside the reaction canister as a residue, so the yield is low and it is complicated to clean the residue.

French Unexamined Patent Application Publication No. 2692263A (Patent Document 4) discloses a method of adding an oligomer of an -hydroxycarboxylic acid or an ester or salt thereof to a solvent containing a catalyst and stirring while heating to achieve catalytic decomposition. This method is performed at normal pressure or increased pressure using a solvent suitable for accompanying a cyclic ester in the gas phase, and the gas is condensed to recover the cyclic ester and the solvent. In this document, an example using a lactic acid oligomer and dodecane (boiling point: approximately 214° C.) as a solvent is illustrated. However, when the present inventors conducted additional tests under the same conditions using a glycolic acid oligomer and dodecane, the formation of heavy material progressed simultaneously with the initiation of the depolymerization reaction, and the production of glycolide stopped at a point when only a very small amount of glycolide had been produced. Moreover, the reaction residue was viscous, and cleaning required a substantial amount of labor.

Japanese Unexamined Patent Application Publication No. H9-328481A (Patent Document 5) discloses a method of using a high-boiling-point polar organic solvent in a method for producing a dimeric cyclic ester of -hydroxycarboxylic acid by depolymerizing an -hydroxycarboxylic acid oligomer. This production method is a method of heating a mixture containing from 30 to 5,000 parts by weight of a high-boiling-point polar organic solvent per 100 parts by weight of an -hydroxycarboxylic acid oligomer to a temperature at which depolymerization occurs so as to form an essentially uniform solution phase, further continuing heating at the same temperature to distill out the dimeric cyclic ester that is produced together with the high-boiling-point polar organic solvent, and then recovering the dimeric cyclic ester from the distillate. With this method, it is possible to obtain a dimeric cyclic ester from an -hydroxycarboxylic acid oligomer with high yield while preventing the oligomer from becoming a heavy material.

Patent Document 5 cites multiple polar organic solvents with a boiling point within the range of from 230 to 450° C. as high-boiling-point polar organic solvents, but the solvents which were specifically used and in working examples and for which effects were confirmed are the aromatic ester compounds di(2-methoxyethyl)phthalate, diethylene glycol dibenzoate or benzyl butyl phthalate, dibutyl phthalate, and tricresyl phosphate. When the present inventors further investigated depolymerization reactions using these aromatic ester compounds as high-boiling-point polar organic solvents, it became clear that when heated for a long period of time to a temperature at which the depolymerization of a glycolic acid oligomer occurs, the aromatic ester compounds tend to cause thermal degradation. When an aromatic ester compound thermally undergoes thermal degradation, a purification step becomes necessary to reuse the compound as a solvent. In addition, in a depolymerization reaction, a necessity arises to add an amount corresponding to the amount of the degraded aromatic ester compound. As a result, it is difficult to further reduce the production cost of a dimeric cyclic ester.

Further, there have been practically no proposed conventional methods for producing a glycolide primarily using a glycolic acid oligomer as a starting raw material for depolymerization and using a polyglycolic acid with a high molecular weight. Japanese Unexamined Patent Application Publication No. 2000-119269 (Patent Document 6) proposes a method for producing a glycolide in which a polyglycolic acid is subjected to solid-phase depolymerization within a temperature range of 200° C. or higher and less than 245° C. However, this method is not necessarily suitable as a method for mass-producing a glycolide efficiently on an industrial scale. In addition, with this method, the polyglycolic acid tends to become heavy when the heating temperature is not strictly controlled.

The present inventors have proposed a method for producing a cyclic ester as WO/2002/14303 (Patent Document 7), wherein:

(I) a mixture containing an aliphatic polyester and a polyalkylene glycol ether, which is expressed by the following formula:

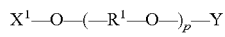

$$X^1-O-(-R^1-O-)_p-Y$$

(wherein $R^1$ is a methylene group or a straight-chain or branched alkylene group having from 2 to 8 carbon atoms, $X^1$ is a hydrocarbon group, Y is an alkyl group or an aryl group having from 2 to 20 carbon atoms, p is an integer of 1 or greater, and when p is 2 or greater, a plurality of $R^1$ moieties may be the same or different from one another); and has a boiling point of from 230 to 450° C. and a molecular weight of from 150 to 450, is heated to a temperature at which the depolymerization of the aliphatic polyester occurs at normal pressure or reduced pressure;

(II) a substantially uniform solution phase is formed in which a melt phase of the aliphatic polyester and a liquid phase consisting of the polyalkylene glycol ether;

(III) heating is continued in the solution state so as to produce the cyclic ester by depolymerization and distill out the cyclic ester together with the polyalkylene glycol ether; and (IV) a cyclic ester is recovered from the distillate. According to this method, the cyclic ester formed by depolymerization is distilled off together with the polyalkylene glycol ether and both compounds are separated into distinct liquid phases to recover the cyclic ester phase, while the polyalkylene glycol ether phase without thermal deterioration may be circulated to the reaction system of depolymerization for its reuse. In the method described in Patent Document 7, a polyalkylene glycol ether is used at a ratio of ordinarily from 30 to 500 parts by weight and preferably from 50 to 200 parts by weight per 100 parts by weight of the aliphatic polyester, and in a specific example, from 450 to 1,000 parts by weight of a polyalkylene glycol ether is used per 100 parts by weight of the aliphatic ester. Therefore, in order to distill out the cyclic ester produced by depolymerization together with the polyalkylene glycol ether, a large amount of thermal energy is required, so there has been a demand for further improvements.

Polyglycolic acid is expected to be mass-produced and used in large quantities in the future, and the recycling of the product waste will be a critical issue. The recycling of mold wastes produced as a by-product at the time of the molding of polyglycolic acid will also become an issue. If a glycolide could be produced by depolymerizing a polyglycolic acid, it would become easy to recycle the polyglycolic acid.

CITATION LIST

Patent Literature

Patent Document 1: U.S. Pat. No. 2,668,162
Patent Document 2: U.S. Pat. No. 4,835,293
Patent Document 3: U.S. Pat. No. 5,023,349
Patent Document 4: French Unexamined Patent Application Publication No. 2692263
Patent Document 5: Japanese Unexamined Patent Application Publication No. H9-328481 (corresponding to U.S. Pat. No. 5,830,991)
Patent Document 6: Japanese Unexamined Patent Application Publication No. 2000-119269A
Patent Document 7: WO/2002/14303 (corresponding to U.S. Patent Application Publication No. 2003/0191326)

SUMMARY OF INVENTION

Technical Problem

The problem of the present invention is to provide a method capable of continuing a reaction for a long period of time without any decrease in production efficiency and efficiently and economically producing a glycolide by depolymerizing a polyglycolic acid.

Solution to Problem

When conducting research in order to achieve the object described above, the present inventors discovered that when the production amount of diglycolic acid, which is a dimer of glycolic acid, is large among the various impurities produced in a polyglycolic acid depolymerization system, the glycolide production efficiency decreases at an early stage, and the depolymerization reaction of the polyglycolic acid stops in a short amount of time.

Upon advancing this research further, the present inventors discovered that the amount of diglycolic acid that is produced decreases when the reaction temperature of the depolymerization reaction of the polyglycolic acid is reduced. It was inferred that if the reaction temperature of the depolymerization reaction of a polyglycolic acid was reduced, then it would be possible to reduce degradation loss of a polyglycolic acid such as a glycolic acid oligomer serving as a raw material for producing a glycolide, or the dissipation loss of the solvent used to execute the depolymerization reaction. One possible method of reducing the reaction temperature of the depolymerization reaction of a polyglycolic acid would be to reduce the pressure of the polyglycolic acid depolymerization reaction system, but this is not preferable since there is an increase in the dissipation loss of the solvent and increases in the amounts of other impurities that are produced, and it has been difficult to provide a method for efficiently and economically producing a glycolide by depolymerizing a polyglycolic acid due to increases in the equipment cost of the vacuum system or the like.

As a result of conducting dedicated research in order to achieve the object described above, the present inventors discovered that by selecting and using a specific polyethylene glycol ether that is not specifically disclosed as a high-boiling-point polar organic solvent in the aforementioned Patent Document 5 or 7, it is possible to reduce the reaction temperature of the depolymerization reaction of a polyglycolic acid without reducing the pressure of the polyglycolic acid depolymerization reaction system. The present inventors thus conceived of the idea that a glycolide can be produced efficiently and economically by depolymerizing a polyglycolic acid, and the present inventors thereby completed the present invention.

That is, the present invention provides
a method for producing a glycolide by depolymerizing polyglycolic acid, the method comprising:
(I) a heating step of heating a mixture either under normal pressure or reduced pressure at a temperature at which a polyglycolic acid (A) undergoes depolymerization, the mixture containing the polyglycolic acid (A) and a polyethylene glycol ether (B) which is represented by the following formula (1):

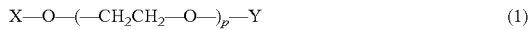

(wherein X and Y are each independently an alkyl group or an aryl group having from 2 to 20 carbon atoms, and p is an integer from 1 to 5)
and which has a molecular weight of from 150 to 450 and a boiling point of from 130 to 220° C. at a pressure of 3 kPa;
(II) a solution-forming step in which the mixture is rendered in a solution state in which a melt phase of the polyglycolic acid (A) and a liquid phase consisting of the polyethylene glycol ether (B) essentially form a uniform phase;
(III) a glycolide production step in which a glycolide is produced by a depolymerization reaction of the polyglycolic acid (A) by continuing to heat the mixture in the solution state;
(IV) a distillation step of distilling off the produced glycolide together with the polyethylene glycol ether (B) from the depolymerization reaction system; and
(V) a recovery step of recovering the glycolide from the distillate.

In addition, the present invention provides the following methods (1) to (20) for producing a glycolide as embodiments.
(1) The method for producing a glycolide described above, wherein the polyethylene glycol ether (B) is a polyethylene glycol ether in which a glycolide solubility at a temperature of 85° C. is from 0.1 to 5 mass %.
(2) The method for producing a glycolide described above, wherein the polyethylene glycol ether (B) is a polyethylene glycol ether in which both X and Y in formula (1) described above are alkyl groups, and a total of a number of carbon atoms of these alkyl groups is from 5 to 28.
(3) The method for producing a glycolide described above, wherein in step (I), the polyethylene glycol ether (B) is mixed at a ratio of from 10 to 100 parts by mass per 100 parts by mass of the polyglycolic acid (A).
(4) The method for producing a glycolide described above, wherein in steps (I) to (III), the mixture is heated to a temperature of from 200 to 232° C.
(5) The method for producing a glycolide described above, wherein in step (III), heating is continued under reduced pressure of from 0.3 to 90 kPa.
(6) The method for producing a glycolide described above, wherein in steps (I) to (III), the mixture further contains a solubilizing agent (C) for increasing a solubility of the polyglycolic acid (A) with respect to the polyethylene glycol ether (B).
(7) The method for producing a glycolide described above, wherein the solubilizing agent (C) is a non-basic compound having a boiling point of 180° C. or higher at normal pressure and having compatibility with the polyethylene glycol ether (B).
(8) The method for producing a glycolide described above, wherein the solubilizing agent (C) is at least one type selected from the group consisting of monohydric, dihydric, or higher polyhydric alcohols, phenols, monohydric, dihydric, or higher polyhydric aliphatic carboxylic acids, aliphatic amides of aliphatic carboxylic acids and amines, aliphatic imides, and polyalkylene glycol ethers having a molecular weight greater than 450.
(9) The method for producing a glycolide described above, wherein the solubilizing agent (C) contains a polyalkylene glycol represented by formula (2):

(wherein $R^1$ is a methylene group or a straight-chain or branched alkylene group having from 2 to 8 carbon atoms, p is an integer of 1 or greater, and when q is 2 or greater, a plurality of $R^1$ moieties may be the same or different from one another).
(10) The method for producing a glycolide described above, wherein the polyalkylene glycol is at least one type selected from the group consisting of polyethylene glycols, polypropylene glycols, and polybutylene glycols.
(11) The method for producing a glycolide described above, wherein the solubilizing agent (C) contains a polyalkylene glycol monoether represented by formula (3):

(wherein $R^2$ is a methylene group or a straight-chain or branched alkylene group having from 2 to 8 carbon atoms, $X^1$ is a hydrocarbon group, r is an integer of 1 or greater, and when r is 2 or greater, a plurality of $R^2$ moieties may be the same or different from one another).
(12) The method for producing a glycolide described above, wherein the polyalkylene glycol monoether is at least one type selected from the group consisting of polyethylene glycol monoethers, polypropylene glycol monoethers, and polybutylene glycol monoethers.

(13) The method for producing a glycolide described above, wherein the polyalkylene glycol monoether has an alkyl group having from 1 to 18 carbon atoms as an ether group thereof.

(14) The method for producing a glycolide described above, wherein the solubilizing agent (C) contains (C1) a monohydric, dihydric, or higher polyhydric alcohol having a boiling point of 180° C. or higher at normal pressure, and (C2) a non-basic compound (excluding monohydric, dihydric, or higher polyhydric alcohols) having a boiling point of 180° C. or higher at normal pressure and having compatibility with the polyethylene glycol ether (B).

(15) The method for producing a glycolide described above, wherein the solubilizing agent (C) is added at a ratio of from 0.1 to 500 parts by mass per 100 parts by mass of the polyglycolic acid (A).

(16) The method for producing a glycolide described above, wherein in step (V), the distillate is cooled with a condenser, the glycolide and the polyethylene glycol ether (B) are phase-separated in a liquid state, and the glycolide phase is separated and recovered.

(17) The method for producing a glycolide described above, wherein the distillate is cooled at a temperature of from 85 to 180° C., and the glycolide and the polyethylene glycol ether (B) are phase-separated in a liquid state.

(18) The method for producing a glycolide described above, wherein phase separation is performed while continuing the depolymerization reaction, and the glycolide in the distillate is condensed in the glycolide phase of the lower layer.

(19) The method for producing a glycolide described above, wherein the polyethylene glycol ether (B) phase is separated and circulated to the depolymerization reaction system.

(20) The method for producing a glycolide described above, wherein the polyethylene glycol ether (B) has a boiling point of from 230 to 450° C. at normal pressure.

Advantageous Effects of Invention

The present invention is
a method for producing a glycolide by depolymerizing polyglycolic acid, the method comprising:
(I) a heating step of heating a mixture either under normal pressure or reduced pressure at a temperature at which a polyglycolic acid (A) undergoes depolymerization, the mixture containing the polyglycolic acid (A) and a polyethylene glycol ether (B) which is represented by the following formula (1):

(wherein X and Y are each independently an alkyl group or an aryl group having from 2 to 20 carbon atoms, and p is an integer from 1 to 5)
and which has a molecular weight of from 150 to 450 and a boiling point of from 130 to 220° C. at a pressure of 3 kPa;
(II) a solution-forming step in which the mixture is rendered in a solution state in which a melt phase of the polyglycolic acid (A) and a liquid phase consisting of the polyethylene glycol ether (B) essentially form a uniform phase;
(III) a glycolide production step in which a glycolide is produced by a depolymerization reaction of the polyglycolic acid (A) by continuing to heat the mixture in the solution state;
(IV) a distillation step of distilling off the produced glycolide together with the polyethylene glycol ether (B) from the depolymerization reaction system; and (V) a recovery step of recovering the glycolide from the distillate.

This yields the effect of providing a method capable of continuing a reaction for a long period of time without any decrease in production efficiency and efficiently and economically producing a glycolide by depolymerizing a polyglycolic acid (A).

DESCRIPTION OF EMBODIMENTS

1. Polyglycolic Acid (A)

The method for producing a glycolide according to the present invention is a method for producing a glycolide by depolymerizing a polyglycolic acid (also called "PGA" hereafter).

The PGA (A) (also simply called "PGA" hereafter) used as a starting raw material in the present invention is a (co)polymer containing repeating glycolic acid units (—O—CH$_2$—CO—) capable of producing a glycolide by means of depolymerization. A PGA can be synthesized in accordance with a conventional method and can be obtained by subjecting glycolic acid, an alkyl ester of glycolic acid, or a salt of glycolic acid to polycondensation in the presence of a catalyst as necessary. In addition a PGA can also be obtained by means of ring-opening (co)polymerization using a glycolide as a monomer.

In the present invention, a PGA is defined as substances including substances with a low molecular weight such as oligomers to substances with a high molecular weight. That is, in the present invention, a PGA with a weight average molecular weight in a range of preferably from 100 to 1,000,000 can be used. The weight average molecular weight is a value measured using gel permeation chromatography (GPC) and can be measured as a standard polymethylmethacrylate (PMMA) reduced value by means of GPC measurement using hexafluoroisopropanol (HFIP) as a solvent.

A PGA with a low molecular weight such as an oligomer and a PGA with a high molecular weight cannot necessarily be distinguished clearly, but in the present invention, a substance with a low molecular weight in which the weight average molecular weight is less than 20,000, preferably from 100 to 19,500, more preferably from 200 to 19,200, in some cases from 500 to 18,000, and further even less than 10,000 may be called an "oligomer" or a "PGA with a low molecular weight such as an oligomer". The degree of polymerization of an oligomer—that is, the number of repeating units of glycolic acid—is ordinarily 2 or higher and preferably 5 or higher. A PGA with a high molecular weight refers to a substance in which the weight average molecular weight is ordinarily 20,000 or higher, preferably from 20,000 to 1,000,000, and more preferably from 30,000 to 800,000.

The PGA may be a copolymer, but in this case, it should be a copolymer in which the content of repeating units of glycolic acid is 50 mass % or higher, preferably 80 mass % or higher, and more preferably 90 mass % or higher.

As described above, a PGA can be synthesized in accordance with a conventional method. More specifically, for example, in order to synthesize a glycolic acid oligomer, a glycolic acid or an ester or salt thereof is heated in the presence of a transesterification catalyst or condensation catalyst as necessary at reduced pressure or increased pressure at a temperature of from 100 to 250° C. and preferably from 140 to 230° C., and a condensation reaction or transesterification reaction is performed until the distillation of low molecular weight substances such as water or alcohol is essentially eliminated. After the condensation reaction or the transesterification reaction is complete, the produced oligomer can be used directly as a raw material for depolymerization according to the present invention. In addition, the obtained oligomer may be extracted from the reaction system, washed with a non-solvent such as benzene or toluene, and used after unreacted matter, catalysts, and the like are removed. The structure of the oligomer may be cyclic or straight-chained. Other glycolic acid oligomers may also be synthesized with the same method.

The oligomer may have a low degree of polymerization, but the melting point (Tm) is ordinarily 140° C. or higher, preferably 160° C. or higher, and more preferably 180° C. or higher from the perspective of the yield of glycolide at the time of depolymerization. Here, Tm is the melting point detected when heated at a rate of 20° C./min in an inert gas atmosphere using a differential scanning calorimeter (DSC).

A PGA with a high molecular weight can be synthesized by the ring-opening (co)polymerization of a glycolide, but waste matter of used products, mold wastes, or the like can be suitably used, and this enables recycling. The shape of a PGA with a high molecular weight is not particularly limited, and any shape such as a sheet shape, a film shape, a thread shape, a spherical shape, a columnar shape, or a rod shape, for example, can be used. It is preferable from the perspective of increasing the reaction efficiency to prepare these products into a granular shape, a powder, or a fiber, or the like prior to a depolymerization reaction. For this purpose, the products can be used in a depolymerization reaction after being granulated or powderized by pulverization, melting, or the like or processed into a fiber shape by melting or drawing.

In the present invention, the PGA may be added all at once into a reactor such as a reaction vessel prior to the reaction, or it may be added by continuous addition or divided addition during the depolymerization reaction. However, as described below, a solution state is established in which a melt phase of the PGA (A) in the reaction vessel and a liquid phase consisting of the polyethylene glycol ether (B) essentially form a uniform phase during the depolymerization reaction. In order to ensure that the melt phase of the PGA (A) and the liquid phase of the polyethylene glycol ether (B) form a more uniform phase, a backup reaction vessel may be provided separately, and the uniform phase may be introduced into the reaction vessel for performing the depolymerization reaction after the uniform phase is formed in the backup reaction vessel. Further, a substantially uniform phase may also be formed by using the solubilizing agent described below in combination with the polyethylene glycol ether (B).

2. Polyethylene Glycol Ether (B)

In the method for producing a glycolide by depolymerizing a PGA according to the present invention, the polyethylene glycol ether (B) used as a solvent of the depolymerization reaction is a polyethylene glycol ether (B) which is represented by the following formula (1):

X—O—(—CH$_2$CH$_2$—O—)$_p$—Y  (1)

(wherein X and Y are each independently an alkyl group or an aryl group having from 2 to 20 carbon atoms, and p is an integer from 1 to 5)
and which has a molecular weight of from 150 to 450 and a boiling point of from 130 to 220° C. at a pressure of 3 kPa.

The polyethylene glycol ether (B) is used as a polar organic solvent for the depolymerization reaction of the PGA (A) and is also used as a polar organic solvent for extracting the produced glycolide from the reaction system.

The polyethylene glycol ether (B) used in the present invention is a diether in which the ether groups at both ends (that is, X and Y) are each independently an alkyl group or an aryl group having from 2 to 20 carbon atoms, preferably from 2 to 18 carbon atoms, and more preferably from 3 to 16 carbon atoms. When the number of carbon atoms of the ether groups (corresponding to X and/or Y) at both ends of the polyethylene glycol ether (B) exceeds 20, the polarity of the polyethylene glycol ether decreases, so it becomes difficult to form a uniform phase with the melt phase of the PGA (A) at the time of the depolymerization reaction.

Even in the case of polyethylene glycol compounds that do not have ether groups at both ends but have a hydroxyl group at an end (polyethylene glycol monoether or the like) or have an ester group at an end (polyethylene glycol ester or the like), using such compounds as polar organic solvents for the depolymerization reaction of the PGA instead of the polyethylene glycol ether (B) may cause thermal degradation during the depolymerization reaction.

In the polyethylene glycol ether (B), the ether groups at both ends—that is, X and Y in the aforementioned formula (1)—are both alkyl groups, and the total number of carbon atoms of these alkyl groups is preferably from 5 to 28, more preferably from 6 to 24, and even more preferably from 6 to 20. Examples of such alkyl groups include propyl groups, butyl groups, pentyl groups, hexyl groups, heptyl groups, octyl groups, nonyl groups, decyl groups, and dodecyl groups (lauryl groups), and these may be used in combination as the ether groups (X and Y) at both ends. These alkyl groups may be straight-chained or branched-chain. When the total number of carbon atoms of the alkyl groups exceeds 28, the molecular weight of the polyethylene glycol ether (B) represented by the aforementioned formula (1) tends to exceed 450, which may inhibit the codistillation with the glycolide at the time of the depolymerization of the PGA (A).

Alkyl groups having the same numbers of carbon atoms such as dibutyl, dihexyl, or dioctyl can be used as the alkyl groups of the ether groups (that is, X and Y) at both ends of the polyethylene glycol ether (B), but the numbers of carbon atoms are not necessarily the same. For example, combinations of different types of alkyl groups such as a propyl group and a lauryl group, a hexyl group and a heptyl group, a butyl group and an octyl group, or a butyl group and a dodecyl group may be used.

When X or Y is an aryl group in the aforementioned formula (1), specific examples of aryl groups include phenyl groups, naphthyl groups, substituted phenyl groups, and substituted naphthyl groups. Here, alkyl groups, alkoxy groups, and halogen atoms (chlorine, bromine, iodine, or the like) are preferable as substituents. When X or Y is a substituted phenyl group, the number of substituents is ordinarily from 1 to 5 and preferably from 1 to 3. When there are a plurality of substituents, the respective substituents may be the same or different from one another. The boiling point and polarity of the polyethylene glycol ether (B) can be adjusted by the types and number of substituents.

The disposition of the polyethylene glycol ether (B) changes depending on the number of repetitions p of ethyleneoxy units (—CH$_2$CH$_2$—O—) in the aforementioned formula (1). In the present invention, a polyethylene glycol ether (B) in which the number of repetitions p is an integer from 1 to 5, preferably 1 to 3, and more preferably 1 or 2 is used. When the number of repetitions p is large, the distribution of the degree of polymerization tends to become wide when an attempt is made to synthesize the polyethylene glycol ether (B) by means of a polyaddition reaction, which makes it difficult to isolate polyethylene glycol ethers (B) having the same numbers of repeating units. In addition, when the number of repetitions p exceeds 5, the obtained polyethylene glycol ether represented by the aforementioned formula (1) assumes a high molecular weight, and as a result, isolation by means of distillation also becomes difficult, which reduces the yield and inhibits codistillation with the glycolide at the time of the depolymerization of the PGA.

(Molecular Weight)

The molecular weight of the polyethylene glycol ether (B) is from 150 to 450. When the molecular weight of the polyethylene glycol ether is too low or too high, codistillation with the glycolide becomes difficult at the time of the depolymerization of the PGA. The molecular weight of the polyethylene glycol ether (B) is preferably within a range of from 180 to 400 and more preferably from 200 to 350.

(Boiling Point at a Pressure of 3 kPa)

The boiling point of the polyethylene glycol ether (B) at a pressure of 3 kPa is from 130 to 220° C. When the boiling point of the polyethylene glycol ether (B) at a pressure of 3 kPa is too low, it is not possible to set the temperature for distilling off the glycolide produced by the depolymerization reaction of the PGA from the depolymerization reaction system together with the polyethylene glycol ether (B) to a high temperature. Therefore, it is necessary to set the PGA depolymerization reaction temperature to a low temperature, which may cause a reduction in the glycolide production rate. On the other hand, when the boiling point of the polyethylene glycol ether (B) at a pressure of 3 kPa is too high, the polyethylene glycol ether (B) becomes difficult to distill off, and codistillation with the glycolide produced by the depolymerization reaction of the PGA may become difficult. The boiling point of the polyethylene glycol ether (B) at a pressure of 3 kPa is preferably within a range of from 135 to 218° C., more preferably from 140 to 216° C., and even more preferably from 145 to 214° C.

(Boiling Point at Normal Pressure)

In addition, the boiling point of the polyethylene glycol ether (B) at normal pressure is not particularly limited but is preferably from 230 to 450° C. When the boiling point of the polyethylene glycol ether (B) at normal pressure is too low, it becomes necessary to set the PGA depolymerization reaction temperature to a low temperature, so the glycolide production rate may decrease. On the other hand, when the boiling point of the polyethylene glycol ether (B) at normal pressure is too high, the polyethylene glycol ether (B) becomes difficult to distill off, and codistillation with the glycolide produced by the depolymerization reaction of the PGA (A) may become difficult. The boiling point of the polyethylene glycol ether (B) at normal pressure is preferably within a range of from 240 to 420° C. and more preferably from 250 to 400° C.

(Glycolide Solubility at a Temperature of 85° C.)

The glycolide solubility of the polyethylene glycol ether (B) used in the present invention at a temperature of 85° C. is preferably from 0.1 to 5 mass %. In many cases, the glycolide solubility at a temperature of 85° C. is more preferably from 0.3 to 4.5 mass % and even more preferably from 0.6 to 4 mass %. Here, the glycolide solubility at a temperature of 85° C. is expressed as the percentage of the mass B (g) of the glycolide with respect to the volume A (ml) of the polyethylene glycol ether (B) when dissolved in the polyethylene glycol ether (B) at a temperature of 85° C. until the glycolide reaches a saturated state. That is, the solubility is calculated with the following formula.

Solubility(mass %)=(B/A)×100

When the glycolide solubility at a temperature of 85° C. is too low, the glycolide that is distilled off together with the polyethylene glycol ether (B) is deposited, which tends to cause the plugging of the recovery line or the like and is therefore not preferable. On the other hand, when the glycolide solubility at a temperature of 85° C. is too high, it may become necessary to isolate the glycolide by cooling to a temperature of 0° C. or lower or add a non-solvent, for example, in order to recover the glycolide from the codistillate of the glycolide and the polyethylene glycol ether (B) obtained by the depolymerization reaction of the PGA. A large amount of energy is required to cool to a low temperature on an industrial scale, so the efficiency or economical viability is lost. In addition, the addition of a non-solvent requires the separation of the non-solvent when recovering and reusing the polyethylene glycol ether (B), which is disadvantageous for industrialized mass production since the number of processes and the amount of equipment increase.

Further, the glycolide solubility of the polyethylene glycol ether (B) used in the present invention at a temperature of 25° C. (normal temperature) is preferably 0.1 mass % or higher. In many cases, the polyethylene glycol ether (B) preferably has a glycolide solubility of from 0.1 to 1.5 mass % and more preferably from 0.15 to 1.3 mass %. Here, the glycolide solubility at a temperature of 25° C. is calculated with the same formula as in the case of the solubility at a temperature of 85° C.

Examples of polyethylene glycol ethers (B) having these characteristics include polyethylene glycol dialkyl ethers such as ethylene glycol dibutyl ether, ethylene glycol dihexyl ether, ethylene glycol dioctyl ether, ethylene glycol butyl hexyl ether, ethylene glycol butyl octyl ether, ethylene glycol butyl decyl ether, ethylene glycol butyl dodecyl ether, ethylene glycol hexyl octyl ether, ethylene glycol hexyl decyl ether, ethylene glycol hexyl dodecyl ether, ethylene glycol octyl decyl ether, diethylene glycol diethyl ether, diethylene glycol dipropyl ether, diethylene glycol dibutyl ether, diethylene glycol dihexyl ether, diethylene glycol butyl hexyl ether, diethylene glycol butyl octyl ether, diethylene glycol hexyl octyl ether, triethylene glycol diethyl ether, triethylene glycol dipropyl ether, triethylene glycol dibutyl ether, triethylene glycol dihexyl ether, triethylene glycol butyl hexyl ether, tetraethylene glycol diethyl ether, tetraethylene glycol dipropyl ether, tetraethylene glycol dibutyl ether, and pentaethylene glycol diethyl ether; polyethylene glycol alkyl aryl ethers in which at least one hydrogen atom of the phenyl groups of diethylene glycol butyl phenyl ethers, diethylene glycol hexyl phenyl ethers, or compounds thereof is substituted with an alkyl group, an alkoxy group, a halogen atom, or the like; and polyethylene glycol diaryl ethers in which at least one hydrogen atom of the phenyl groups of diethylene glycol diphenyl ethers, or compounds thereof is substituted with an alkyl group, an alkoxy group, a halogen atom, or the like.

A particularly preferable polyethylene glycol ether (B) is an ethylene glycol dioctyl ether, ethylene glycol butyl octyl ether, ethylene glycol butyl dodecyl ether, diethylene glycol butyl octyl ether, or the like.

Here, a triethylene glycol butyl octyl ether (X and Y are a butyl group and an aryl group, and p=3), which is represented by formula (1)

X—O—(—CH$_2$CH$_2$—O—)$_p$—Y (1)

(wherein X and Y are each independently an alkyl group or an aryl group having from 2 to 20 carbon atoms, and p is an integer from 1 to 5) and which has a molecular weight of from 150 to 450 does not belong to the polyethylene glycol ether (B) of the present invention since the boiling point at a pressure of 3 kPa is 223° C.

The properties of particularly preferable polyethylene glycol ethers (B) and the aforementioned triethylene glycol butyl octyl ether are shown in Table 1.

TABLE 1

X—O—(—CH$_2$CH$_2$—O—)$_p$—Y

| Polyethylene glycol ether | X | C number | Y | C number | P | Molecular weight |
|---|---|---|---|---|---|---|
| Ethylene glycol butyl octyl ether | Bu | 4 | Oct | 8 | 1 | 230 |
| Diethylene glycol butyl octyl ether | Bu | 4 | Oct | 8 | 2 | 274 |
| Ethylene glycol butyl dodecyl ether | Bu | 4 | Dodec | 12 | 1 | 286 |
| Ethylene glycol dioctyl ether | Oct | 8 | Oct | 8 | 1 | 286 |
| Triethylene glycol butyl octyl ether | Bu | 4 | Oct | 8 | 3 | 318 |

| | Boiling point (° C.) | | Glycolide solubility (mass %) | |
|---|---|---|---|---|
| Polyethylene glycol ether | Pressure: 3 kPa | Normal Pressure | Temperature: 85° C. | Temperature: 25° C. |
| Ethylene glycol butyl octyl ether | 163 | 272 | 1.5 | 0.25 |
| Diethylene glycol butyl octyl ether | 199 | 316 | 3.8 | 0.85 |
| Ethylene glycol butyl dodecyl ether | 211 | 306 | 0.95 | 0.19 |
| Ethylene glycol dioctyl ether | 195 | 304 | 0.7 | 0.37 |
| Triethylene glycol butyl octyl ether | 223 | 354 | 5.5 | 1.7 |

(Footnotes)
Bu: butyl group
Oct: octyl group
Dodec: dodecyl group

In the method for producing a glycolide by depolymerizing a PGA according to the present invention, the polyethylene glycol ether (B) is mixed and used at a ratio of normally from 10 to 100 parts by mass, preferably from 12 to 85 parts by mass, more preferably from 13 to 70 parts by mass, even more preferably from 14 to 60 parts by mass, and particularly preferably from 15 to 50 parts by mass per 100 parts by mass of the PGA (A). When the usage ratio of the polyethylene glycol ether (B) is too low, it may become difficult for the melt phase of the PGA (A) and the liquid phase consisting of the polyethylene glycol ether (B) to form a substantially uniform phase, or it may become difficult for the glycolide that is produced by the depolymerization reaction of the PGA (A) to be distilled off together with the polyethylene glycol ether (B). When the usage ratio of the polyethylene glycol ether (B) is too large, the cost of recovering the polyethylene glycol ether (B) also increases, which is not economical.

(Production of Polyethylene Glycol Ether (B))

The polyethylene glycol ether (B) can be obtained by applying a production method for a polyethylene glycol ether that has been widely known to those having ordinary skill in the art prior to the filing of this application. For example, an ethylene glycol diether can be produced by adding ethylene oxide to an alcohol, polyadding the resulting ethylene glycol monoether or ethylene oxide, and subjecting the terminal hydroxy groups of the resulting ethylene glycol ether to etherification. The etherification method is well known and is not particularly limited, but examples typically include a method of reacting a polyethylene glycol monoether with an alkyl halide in the presence of metallic sodium, sodium hydride, sodium hydroxide, or the like; a method of making sodium iodide coexist with this substance at this time; and a method of using a substance prepared by performing sulfonic acid esterification on an alcohol using a chloride sulfonate (for example, tosyl choride, mesyl chloride, or the like) in the presence of a basic compound instead of an alkyl halide (that is, an alkylation agent) as an alkylation agent in the presence of a basic compound instead of an alkyl halide (that is, an alkylation agent).

3. Solubilizing Agent (C)

In steps (I) to (III) in the method for producing a glycolide by depolymerizing a PGA according to the present invention, it is possible to use a mixture further containing a solubilizing agent (C) in order to increase the solubility (specifically, this refers to the solubility and/or solubilization rate) of the PGA (A) such as a glycolic acid oligomer or a polyglycolide with respect to the polyethylene glycol ether (B).

The solubilizing agent (C) used in the present invention is preferably a compound which satisfies any one or more of the following requirements.

(i) The solubilizing agent is a non-basic compound.

Basic compounds such as amines, pyridines, and quinolines may react with the PGA or the glycolide that is produced and are therefore not preferable.

(ii) The solubilizing agent is a compound which is compatible with or soluble in the polyethylene glycol ether (B).

The solubilizing agent may be a liquid or a solid at a normal temperature as long as it is a compound which is compatible with or soluble in the polyethylene glycol ether (B).

(iii) The solubilizing agent is a compound having a boiling point of 180° C. or higher, preferably 200° C. or higher, more preferably 230° C. or higher, and even more preferably 250° C. or higher at normal pressure.

In particular, when a compound in which the boiling point at normal pressure is higher than that of the polyethylene glycol ether (B) used in the depolymerization reaction of the PGA is used as the solubilizing agent (C), the solubilizing agent (C) is not distilled off together with the glycolide and the polyethylene glycol ether (B) or the amount of distillation is very small at the time of the distillation of the glycolide produced by the depolymerization reaction of the PGA, which is preferable. In many cases, good results can be obtained by using a compound in which the boiling point at normal temperature is 400° C. or higher, 450° C. or higher, or, depending on the situation, 470° C. or higher as the solubilizing agent (C). However, even in the case of a compound in which the boiling point at normal pressure is lower than that of the polyethylene glycol ether (B) used for depolymerization, alcohols or the like may be suitably used as the solubilizing agent (C).

(iv) The solubilizing agent is, for example, a compound having a functional group such as an OH group, a COOH group, or a CONH group.

(v) The solubilizing agent is a compound having higher affinity with the PGA (A) than the polyethylene glycol ether (B).

The affinity of the solubilizing agent (C) and the PGA (A) can be confirmed by the following method. Specifically, a) a mixture of the PGA (A) and the polyethylene glycol ether (B) is heated to a temperature of from 230 to 280° C. to form a uniform solution phase; b) the PGA (A) is further added to the mixture, and the concentration is increased until the mixture no longer forms a uniform solution phase; and c) a solubilizing agent is added to the mixture, and it is visually observed whether a uniform solution phase is once again formed.

A specific example of a solubilizing agent (C) that can be used in the present invention is a non-basic compound having a boiling point of 180° C. or higher at normal pressure and having compatibility with the polyethylene glycol ether (B).

In addition, specific examples of solubilizing agents (C) that can be used in the present invention include monohydric, dihydric, or higher polyhydric alcohols (may be a partially esterified product or a partially etherified product of a polyhydric alcohol), phenols, monohydric, dihydric, or higher polyhydric aliphatic carboxylic acids, aliphatic amides of aliphatic carboxylic acids and amines, aliphatic imides, and polyalkylene glycol ethers having a molecular weight of over 450. These may be respectively used alone or in combinations of two or more types.

Of these, monohydric, dihydric, or higher polyhydric alcohols are particularly effective as solubilizing agents (C). A monohydric, dihydric, or higher polyhydric alcohol having a boiling point of 180° C. or higher (solubilizing agent (C1)) can be preferably used as a monohydric, dihydric, or higher polyhydric alcohol. The boiling point of the solubilizing agent (C1) at normal pressure is more preferably 200° C. or higher, even more preferably 230° C. or higher, and particularly preferably 250° C. or higher. Examples of solubilizing agents (C) that can be used as the solubilizing agent (C1) include aliphatic alcohols such as decanol, tridecanol, decanediol, ethylene glycol, propylene glycol, and glycerin; aromatic alcohols such as cresol, chlorophenol, and naphthyl alcohol; polyalkylene glycols; and polyalkylene glycol monoethers. Of these, a preferable solubilizing agent (C) is a polyalkylene glycol or a polyalkylene glycol monoether.

An example of a polyalkylene glycol serving as the aforementioned preferable solubilizing agent (C) is a polyalkylene glycol represented by formula (2):

HO—(—R$^1$—O—)$_q$—H     (2)

(wherein R$^1$ is a methylene group or a straight-chain or branched-chain alkylene group having from 2 to 8 carbon atoms, q is an integer of 1 or greater, and when q is 2 or greater, a plurality of R$^1$ moieties may be the same or different from one another).

Specific examples of such polyalkylene glycols include polyethylene glycol, polypropylene glycol, and polybutylene glycol. These may be respectively used alone or in combinations of two or more types.

In addition, an example of a polyalkylene glycol monoether serving as the aforementioned preferable solubilizing agent (C) is a polyalkylene glycol monoether represented by formula (3):

HO—(—R$^2$—O—)$_r$—X$^1$     (3)

(wherein R$^2$ is a methylene group or a straight-chain or branched-chain alkylene group having from 2 to 8 carbon atoms, X$^1$ is a hydrocarbon group, r is an integer of 1 or greater, and when r is 2 or greater, a plurality of R$^2$ moieties may be the same or different from one another).

Specific examples of such polyalkylene glycol monoethers include polyethylene glycol monoethers such as polyethylene glycol monomethyl ether, polyethylene glycol monopropyl ether, polyethylene glycol monobutyl ether, polyethylene glycol monohexyl ether, polyethylene glycol monooctyl ether, polyethylene glycol monodecyl ether, and polyethylene glycol monolauryl ether; a polypropylene glycol monoether in which an ethyleneoxy group is substituted with a propyleneoxy group in the polyethylene glycol monoether; a polybutylene glycol monoether in which an ethyleneoxy group is substituted with a butyleneoxy group in the polyethylene glycol monoether; and other polyalkylene glycol monoethers. A polyalkylene glycol monoether such as a polyethylene glycol monoether preferably has an alkyl group having from 1 to 18 carbon atoms and more preferably has an alkyl group having from 3 to 16 carbon atoms as an ether group. These may be respectively used alone or in combinations of two or more types.

When polyalkylene glycols or polyalkylene glycol monoethers are used as solubilizing agents (C), practically none of the compounds are distilled out of the depolymerization reaction system because of the high boiling points thereof. Moreover, polyalkylene glycols and polyalkylene glycol monoethers have high PGA solubility, so when these are used as solubilizing agents (C), the depolymerization reaction of the PGA may proceed rapidly. In addition, when a polyalkylene glycol monoether is used as a solubilizing agent (C), the cleaning effect of the reactor wall (inner wall of the reactor) is particularly excellent.

Further, in the present invention, a non-basic compound having a boiling point of 180° C. or higher at normal pressure and having compatibility with the polyethylene glycol ether (B) (excluding monohydric, dihydric, or higher polyhydric alcohols) (solubilizing agent (C2)) may be used as a solubilizing agent (C) alone or together with the solubilizing agent (C1). As described above, examples of solubilizing agents (C) that can be used as the solubilizing agent (C2) include phenols, monohydric, dihydric, or higher polyhydric aliphatic carboxylic acids, aliphatic amides of aliphatic carboxylic acids and amines, aliphatic imides, and polyalkylene glycol ethers having a molecular weight of over 450.

A polyalkylene glycol ether having a molecular weight of preferably greater than 450 can be used as the solubilizing agent (C2). That is, in the present invention, a polyalkylene glycol ether having higher affinity with the PGA, a higher molecular weight of greater than 450, and a higher boiling point than the polyethylene glycol ether (B) used as a polar organic solvent for the depolymerization reaction of the PGA can be preferably used as the solubilizing agent (C2). Specific examples of polyalkylene glycol ethers which are suitable as solubilizing agents (C2) include polyethylene glycol dimethyl ether #500 (number average molecular weight: 500) and polyethylene glycol dimethyl ether #2000 (number average molecular weight: 2,000). These polyalkylene glycol ethers serving as solubilizing agents (C2) can be differentiated from the polyethylene glycol ether (B) of the present invention having a molecular weight of from 150 to 450 in that the molecular weight is greater than 450.

The effects of the solubilizing agent (C) are not sufficiently clear, but it is presumed that the solubilizing agent yields effects such as an effect of transforming the PGA into a substance that is easily dissolved in the polyethylene glycol ether (B), an effect of transforming the PGA into a substance that is easily dissolved in the polyethylene glycol ether (B) by severing molecular chains and adjusting the molecular weight in accordance with interactions between the molecular chains of the PGA, an effect of changing the polarity of the entire solvent system so as to increase the affinity and the solubility of the PGA, an effect of emulsifying and dispersing the PGA, or a composite effect of these effects. It is preferable to use a solubilizing agent (C) containing (C1) a monohydric, dihydric, or higher polyhydric alcohol having a boiling point of 180° C. or higher at normal pressure and/or (C2) a non-basic compound (excluding monohydric, dihydric, or higher polyhydric alcohols) having a boiling point of 180° C. or higher at normal pressure and having compatibility with the polyethylene glycol ether (B) as the solubilizing agent (C). In particular, when the solubilizing agent (C) contains a solubilizing agent (C1) and a solubilizing agent (C2), it is possible to perform depolymerization in an even more uniform molten state, which is more preferable.

When a solubilizing agent (C) is used together with the polyethylene glycol ether (B) in the method for producing a glycolide by depolymerizing a PGA according to the present invention, the solubilizing agent (C) is used at a ratio of normally from 0.1 to 500 parts by mass, preferably from 1 to 300 parts by mass, and more preferably from 10 to 150 parts by mass per 100 parts by mass of the PGA (A). When the ratio of the solubilizing agent (C) that is used is too small, the solubility-improving effect of the solubilizing agent (C) cannot be sufficiently achieved. When the ratio of the solubilizing agent (C) that is used is too large, the recovery of the solubilizing agent (C) becomes expensive, which is not economical. When the solubilizing agent (C) uses a solubilizing agent (C1) and a solubilizing agent (C2) in combination, the ratio of the solubilizing agent (C1) and the solubilizing agent (C2) that are used is not particularly limited but is ordinarily set to a ratio (mass ratio) of from 1:99 to 99:1, preferably from 10:90 to 90:10, more preferably from 30:70 to 85:15, and even more preferably from 50:50 to 80:20.

4. Catalyst

In the method for producing a glycolide by depolymerizing a PGA according to the present invention, the PGA dissolves in the polyethylene glycol ether (B), and the surface area thereof expands dramatically, so the glycolide generation rate or volatilization rate by depolymerization is large. Accordingly, it is typically unnecessary to use a catalyst (for example, a tin compound, an antimony compound, or the like) for depolymerization. In the production method of the present invention, which uses a polyethylene glycol ether (B) having excellent thermal stability, there is a risk that the catalyst may actually be harmful. However, a catalyst may also be used within a range that does not essentially diminish the "solution phase depolymerization method" of the present invention.

5. Method for Producing Glycolide by Depolymerizing Polyglycolic Acid

The method for producing a glycolide by depolymerizing a PGA according to the present invention comprises the following steps:

(I) a heating step of heating a mixture either under normal pressure or reduced pressure at a temperature at which a PGA (A) undergoes depolymerization, the mixture containing the PGA (A) and a polyethylene glycol ether (B) which is represented by the formula (I) and which has a molecular weight of from 150 to 450 and a boiling point of from 130 to 220° C. at a pressure of 3 kPa;

(II) a solution-forming step in which the mixture is rendered in a solution state in which a melt phase of the PGA (A) and a liquid phase consisting of the polyethylene glycol ether (B) essentially form a uniform phase;

(III) a glycolide production step in which a glycolide is produced by a depolymerization reaction of the PGA (A) by continuing to heat the mixture in the solution state;

(IV) a distillation step of distilling off the produced glycolide together with the polyethylene glycol ether (B) from the depolymerization reaction system; and (V) a recovery step of recovering the glycolide from the distillate.

The method for producing a glycolide according to the present invention is characterized in that the depolymerization of the PGA is performed in the state of a solution phase using a specific solvent—that is, the polyethylene glycol ether (B). The depolymerization reaction of a PGA is ordinarily performed at a temperature of 200° C. or higher, but when most of the PGA forms a melt phase without dissolving in the solvent, the glycolide is difficult to distill out, and the melt phase tends to become heavy. By continuing to heat the mixture in a solution state in which the melt phase of the PGA and the liquid phase consisting of the polyethylene glycol ether (B) form a substantially uniform phase, the glycolide generation and distillation rates increase dramatically.

In the method for producing a glycolide according to the present invention, a mixture containing the PGA (A) serving as a depolymerization composition and the polyethylene glycol ether (B) is obtained by first introducing the PGA (A) in a melt state or a solid state pulverized into an appropriate particle size as necessary, into a reactor (flask or the like), and then mixing it with the polyethylene glycol ether (B) serving as a solvent in the reactor. When the solubility with respect to the polyethylene glycol ether (B) serving as a solvent is low due to a high molecular weight of the PGA (A), for example, a solubilizing agent (C) may be added to the reactor so as to form a mixture further containing a solubilizing agent (C) for increasing the solubility of the PGA (A) with respect to the polyethylene glycol ether (B). In this case, the solubilizing agent (C) may be one type or a combination of two or more types and may contain, for example, a solubilizing agent (C) containing (C1) a monohydric, dihydric, or higher polyhydric alcohol having a boiling point of 180° C. or higher at normal pressure and/or (C2) a non-basic compound (excluding monohydric, dihydric, or higher polyhydric alcohols) having a boiling point of 180° C. or higher at normal pressure and having compatibility with the polyethylene glycol ether (B). A heater (electric heating device or the like) is installed around the reactor, and the temperature of the reactor and the depolymerization composition inside the reactor can be regulated by adjusting the heating current, for example. In addition, a cooler (condenser) capable of cooling with cold water, for example, may be connected to the reactor in order to cool the distilled components.

[Heating Step]

In the heating step (I), after a mixture (depolymerization composition) containing prescribed amounts of the PGA (A), the polyethylene glycol ether (B), and the solubilizing agent (C) which is added as necessary is heated as necessary for the purpose of dehydration at normal pressure or reduced pressure, it is heated to a temperature at which the depolymerization of the PGA (A) occurs—that is, ordinarily approximately 190° C. or higher, preferably approximately from 200 to 232° C., more preferably approximately from 205 to 230° C., and particularly preferably approximately from 210 to 228° C. The heating step (I) is preferably performed in an inert gas atmosphere such as nitrogen gas and is ordinarily performed at normal pressure, but when depressurization is performed, the pressure is within a range of approximately from 50 to 100 kPa.

(Solution Forming Step)

All or most of the PGA (A) is melted by the heating step (I) so as to form a melt phase, and a solution-forming step (II) is then performed so as to render a solution state in which the melt phase is dissolved in a liquid phase consisting of the polyethylene glycol ether (B) and the solubilizing agent (C) which is added as necessary so as to form a substantially uniform phase. The temperature at which the solution-forming step (II) is performed is preferably maintained at approximately the same level as the temperature at which the mixture is heated in the heating step (I). In the solution-forming step (II), it is preferable for the PGA (A), the polyethylene glycol ether (B), and the solubilizing agent (C) which is added as necessary to form a completely uniform phase, but the PGA melt phase may also be present as long as the residual rate of the PGA melt phase is 0.5 or lower. Here, the "residual rate of the melt phase" refers to a value represented by the ratio b/a, where (a) (ml) is the volume of the PGA (A) melt phase formed when F(g) of the PGA (A) is added to a solvent with essentially no solvent power with respect to the PGA such as liquid paraffin and heated to a temperature at which depolymerization occurs, and (b) (ml) is the volume of the PGA (A) melt phase formed when F(g) of the PGA (A) is heated to a temperature at which depolymerization occurs in the solvent which is actually used. Here, the solvent that is actually used refers to the use of the polyethylene glycol ether (B) alone or the combined use of the polyethylene glycol ether (B) and the solubilizing agent (C). The residual rate of the PGA (A) melt phase is preferably at most 0.3, more preferably at most 0.1, and most preferably substantially zero.

(Glycolide Production Step and Distillation Step)

Next, a glycolide production step (III) is performed, whereby a glycolide is produced by a depolymerization reaction of the PGA (A) by continuing to heat the mixture in a solution state in which the PGA (A), the polyethylene glycol ether (B), and the solubilizing agent (C) which is further contained as necessary form a substantially uniform liquid phase. At the same time, a distillation step (IV) of distilling off the produced glycolide together with the polyethylene glycol ether (B) from the depolymerization reaction system is performed. The codistillation temperature is determined by the composition of the glycolide and the polyethylene glycol ether (B) to be distilled off, so the distillation rate (referring to the amount of distillation per unit time) of the polyethylene glycol ether (B) serving as a solvent can be adjusted by adjusting the amount of heat supplied to the depolymerization reaction system in the reactor by controlling the heating current, for example.

[Recovery step] Next, the glycolide is recovered from the distillate in the recovery step (V). That is, the glycolide can be easily separated and recovered from the distillate by cooling the distillate containing the glycolide (the melting point of the glycolide at normal pressure is approximately 85° C.) and adding a non-solvent of the glycolide as necessary. The recovered glycolide can be purified as necessary by means of recrystallization or the like. On the other hand, the mother liquor from which the glycolide is removed contains the polyethylene glycol ether (B), and since the mother liquor has excellent thermal stability, practically the entire amount can be reused without utilizing a purification step or the like. The polyethylene glycol ether (B) may be reused after being purified by adsorption with activated carbon or the like or purified by distillation or the like.

(Temperature and Pressure of Each Step)

The temperature at which the glycolide production step (III) and the distillation step (IV) described above are performed may be the same as the temperature at which the heating step (I) and the solution-forming step (II) are performed. In this case, in steps (I) to (III), the mixture is preferably heated to a temperature of approximately from 200 to 232° C., more preferably approximately from 205 to 230° C., and particularly preferably approximately from 210 to 228° C. The temperature at which the glycolide production step (III) and the distillation step (IV) are performed may differ from the temperature at which the heating step (I) and the solution-forming step (II) are performed, but the mixture is preferably heated to a temperature of approximately from 200 to 232° C., more preferably approximately from 205 to 230° C., and particularly preferably approximately from 210 to 228° C. In addition, the temperature at which steps (III) and (IV) are performed may also be higher than the temperature at which steps (I) and (II) are performed.

The heating in any of the steps may be performed at normal pressure or reduced pressure. It is preferable for steps (I) and (II) to be performed at normal pressure and then for the glycolide to be distilled off together with the polyethylene glycol ether (B) by heating at reduced pressure in steps (III) and (IV). The depolymerization reaction is a reversible reaction, so the depolymerization reaction of the PGA progresses efficiently when glycolide is distilled out of the liquid phase. In the glycolide production step (III), the pressure at which depolymerization reaction is performed is preferably a reduced pressure of from 0.3 to 90 kPa, and depressurizing to a pressure of preferably from 2 to 50 kPa, more preferably from 2.5 to 15 kPa, and particularly preferably from 3 to 10 kPa makes it possible to increase the distillation efficiency of the glycolide and the polyethylene glycol ether (B) without increasing the depolymerization temperature. That is, reducing the pressure of the depolymerization reaction system typically makes it possible to reduce the temperature at which the glycolide production step (III) and the distillation step (IV) are performed, so the solvent loss decreases, and the recovery rate of the solvent also increases. However, even when the pressure of the depolymerization reaction system is set to less than 0.3 kPa, the effect of improving the distillation efficiency of the glycolide and the polyethylene glycol ether (B) does not increase, whereas the costs associated with designing and maintaining the device tend to rise sharply.

In the present invention, by using the polyethylene glycol ether (B) as a solvent for the depolymerization reaction of the PGA (A), it is possible to suitably perform the glycolide production step (III) and the distillation step (IV) while combining conditions with a pressure of from 3 to 10 kPa, particularly preferably a pressure of from 3.6 to 7 kPa, and most preferably from 4 to 6.8 kPa and conditions with a temperature of from 200 to 232° C., particularly preferably from 210 to 230° C., and in some cases from 215 to 228° C.

In the present invention, the glycolide (boiling point at normal pressure: 240 to 241° C.) is distilled off together with the polyethylene glycol ether (B) so as to prevent situations in which the production of glycolide cannot be continued over a long period of time due to the deposition of glycolide on the inside wall of the distillation line, or situations in which the amount of recovered glycolide decreases—that is, the loss of the PGA (A) increases.

As described above, the polyethylene glycol ether (B) is mixed and used at a ratio of normally from 10 to 100 parts by mass, preferably from 12 to 85 parts by mass, more preferably from 13 to 70 parts by mass, even more preferably from 14 to 60 parts by mass, and particularly preferably from 15 to 50 parts by mass per 100 parts by mass of the PGA (A). The polyethylene glycol ether (B) may be added continuously or in a divided manner during the course of the depolymerization reaction within a range so that the mixture in the depolymerization reaction system forms a substantially uniform liquid phase. In addition, the solubilizing agent (C) may be added continuously or in a divided manner during the course of the depolymerization reaction.

Since the polyethylene glycol ether (B) used in the present invention is chemically and thermally stable in the depolymerization reaction, the amount of the new polyethylene glycol ether (B) that needs to be added at the time of reuse is very small. In addition, since the polyethylene glycol ether (B) has excellent thermal stability, in the recovery step (V) of recovering the glycolide from the distillate, it is possible to phase-separate the distillate while in a liquid state so as to separate and recover the glycolide phase and circulate the polyethylene glycol ether (B) phase to the depolymerization reaction system.

Specifically, the distillate is cooled with a cooler (condenser) so as to phase-separate the glycolide and the polyethylene glycol ether (B) while in a liquid state and to separate and recover the glycolide phase. When the distillate is subjected to phase separation, a glycolide phase is ordinarily formed on the lower layer, and the upper layer becomes a solvent phase (polyethylene glycol ether (B) phase). The glycolide phase of the lower layer can be separated and recovered in the liquid state. In order to perform phase separation on the glycolide and the solvent in the liquid state, the cooling temperature of the distillate is ordinarily adjusted to a range of from 85 to 180° C., preferably from 85 to 150° C., and more preferably from 85 to 120° C. When the cooling temperature is too high, side reactions such as a ring-opening reaction or a polymerization reaction tend to occur in the glycolide phase during the separation operation. When the cooling temperature is too low, it becomes difficult to perform phase separation in the liquid state.

When the temperature of the distillate is adjusted by the condenser and phase separation is performed while continuing the depolymerization reaction of the PGA, the glycolide that is distilled off together with the solvent can pass through the solvent phase of the upper layer (polyethylene glycol ether (B) phase) in the form of liquid droplets and can be condensed in the glycolide phase of the lower layer.

The separated glycolide phase is further cooled, recovered, and then purified as necessary. With this method, the need to separate a large amount of the solvent (polyethylene glycol ether (B)) from the recovered glycolide is eliminated, which simplifies the operation for separating the solvent and the glycolide.

In addition, in this method, the polyethylene glycol ether (B) phase can be separated from the phase-separated distillate and returned to the depolymerization reaction system so as to be circulated. With this method, the need to recover a large amount of the solvent (polyethylene glycol ether (B)) is eliminated, and the need to prepare a solvent in excess of the amount determined by the volume of the reactor is further eliminated. Accordingly, with this method, the loss of the solvent can be kept to a minimum.

When the present invention is a method for producing a glycolide by depolymerizing a PGA (A) with a high molecular weight, it is a method for producing a glycolide comprising:

(i) a heating step of heating a mixture either under normal pressure or reduced pressure at a temperature at which a PGA (A) undergoes depolymerization, the mixture containing the PGA (A);
a polyethylene glycol ether (B) which is represented by the following formula (1):

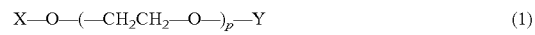

$$X\text{—}O\text{—}(\text{—}CH_2CH_2\text{—}O\text{—})_p\text{—}Y \qquad (1)$$

(wherein X and Y are each independently an alkyl group or an aryl group having from 2 to 20 carbon atoms, and p is an integer from 1 to 5)
and which has a molecular weight of from 150 to 450 and a boiling point of from 130 to 220° C. at a pressure of 3 kPa; and
a solubilizing agent (C) containing (C1) a monohydric, dihydric, or higher polyhydric alcohol having a boiling point of 180° C. or higher at normal pressure and/or (C2) a non-basic compound (excluding monohydric, dihydric, or higher polyhydric alcohols) having a boiling point of 180° C. or higher at normal pressure and having compatibility with the polyethylene glycol ether (B);

(ii) a solution-forming step in which the mixture is rendered in a solution state in which a melt phase of the PGA (A) and a liquid phase consisting of the polyethylene glycol ether (B) and the solubilizing agent (C) essentially form a uniform phase;

(iii) a glycolide production step in which a glycolide is produced by a depolymerization reaction of the PGA (A) by continuing to heat the mixture in the solution state at reduced pressure;

(iv) a distillation step of distilling off the produced glycolide together with the polyethylene glycol ether (B) from the depolymerization reaction system; and (v) a recovery step of recovering the glycolide from the distillate.

Here, the gists or conditions of the heating step (i), the solution-forming step (ii), the glycolide production step (iii), the distillation step (iv), and the recovery step (v) are as described above.

With the method for producing a glycolide according to the present invention, it is possible to start the depolymerization reaction of the PGA at a lower temperature than that of the temperature conditions used conventionally, so it is possible to suppress the production of diglycolic acid in the reaction solution, which causes a rapid decrease in the glycolide production rate in the PGA depolymerization reaction system, the depolymerization reaction of the PGA and the glycolide production reaction to stop in a short period of time. As a result, it is possible to continue the depolymerization of the PGA for a long period of time, which makes it possible to efficiently and economically produce a glycolide.

(Glycolide Production Rate)

The glycolide production rate (also called the "GL production rate" hereafter) in the PGA depolymerization reaction system is determined by the following method. Specifically, the distillate (glycolide and solvent) that is distilled off in one hour immediately after the depolymerization reaction is begun (initial stage) or in the first one hour after a prescribed amount of time has passed is cooled with warm water at a temperature of 85° C. so as to separate the glycolide and the solvent. A glycolide phase is ordinarily formed on the lower layer, and the upper layer is a solvent phase. The glycolide phase of the lower layer can be separated and recovered in a liquid state, and the mass (g) of the recovered glycolide is measured. The GL production rate (units: g/hour) immediately after the depolymerization reaction is begun or at a point after a prescribed amount of time has passed is calculated from the mass (g) of the recovered glycolide. For example, the degree of progression of the depolymerization of the PGA can be grasped by using the glycolide and solvent that are distilled off in one hour immediately after the depolymerization reaction is begun (initial stage) and in the first one hour after 10 days have passed, after 20 days have passed, and after 30 days have passed, respectively, after the depolymerization reaction is begun, and determining the GL production rate immediately after the depolymerization reaction is begun (initial stage) and at points after 10 days have passed, after 20 days have passed, and after 30 days have passed after the depolymerization reaction is begun.

(Diglycolic Acid Concentration in Reaction Solution)

The diglycolic acid concentration in the PGA depolymerization reaction solution is measured by the following method. Specifically, a reaction solution in the reactor is collected immediately after the depolymerization reaction is begun (initial stage) or when a prescribed amount of time has passed, and the diglycolic acid concentration in the reaction solution is measured by liquid chromatography. For example, the degree of the production of diglycolic acid as an impurity in the PGA depolymerization reaction system can be grasped by measuring the diglycolic acid concentration (called the "DGA concentration" hereafter) when 10 days have passed, when 20 days have passed, and when 30 days have passed after the depolymerization reaction is begun as the prescribed amounts of time after the depolymerization reaction is begun. When the DGA concentration after 30 days have passed after the depolymerization reaction is begun is at most 5%, preferably at most 4.6%, and more preferably 4.4%, there is a minimal risk that the production of the glycolide by the depolymerization of the PGA will be inhibited in a short period of time by the production of diglycolic acid. The lower limit of the DGA concentration when 30 days have passed is 0%.

With the method for producing a glycolide according to the present invention, practically no PGA (A) is produced in a heavy form at the time of heating and at the time of depolymerization (heating step, glycolide-production step, and distillation step), so the trouble of cleaning inside the reactor can be eliminated. In addition, if heavy material adheres to the inside of the reactor due to some kind of trouble or the like, it can be easily cleaned by placing the polyethylene glycol ether (B) and the solubilizing agent (C) (preferably the solubilizing agent (C1) or the solubilizing agent (C2)) in the reactor and heating.

When the mother liquor from which the glycolide is separated contains the polyethylene glycol ether (B) serving as a solvent or the solubilizing agent (C), the separated mother liquor can be recycled and used directly without purification, recycled and used after adsorption and purification with activated carbon or the like, or recycled and used as the polyethylene glycol ether (B) and/or the solubilizing agent (C) by simple distillation or fractionation. The solubilizing agent (C) has an effect on the solubility of heavy material, so the cleaning inside the reactor can be omitted or reduced in the case of depolymerization using the solubilizing agent (C).

(Polyglycolic Acid Loss Rate after 10 Days)

In addition, with the method for producing a glycolide according to the present invention, the polyglycolic acid loss rate after 10 days (also called the "PGA loss rate after 10 days" hereafter) is small, which makes it possible to continue glycolide production over a long period of time and also contributes to the improvement of original units. The PGA loss rate after 10 days (units: mass %) is calculated by the following formula based on the ratio of the total of the amount of all glycolide that is distilled off and the amount of polyglycolic acid in the reaction solution (that is, the amount of polyglycolic acid remaining in the reaction solution when the depolymerization reaction is ended) with respect to the amount of all of the polyglycolic acid introduced during the period in which the depolymerization reaction of the polyglycolic acid is continued for 10 days (units: g; same hereafter).

PGA loss rate(mass %)=100−((amount of all distilled glycolide+amount of polyglycolic acid in reaction solution)/amount of all introduced polyglycolic acid)×100 (Formula)

With the method for producing a glycolide according to the present invention, the PGA loss rate after 10 days can be set to at 18 mass % or lower and preferably 17 mass % or lower, and it may be set to 16.5 mass % or lower depending on the combination of the polyethylene glycol ether (B) and the solubilizing agent (C) or the selection of the conditions of steps (I) to (III).

6. Operation

The method for producing a glycolide according to the present invention is a method that should be considered a "solution phase depolymerization method", so to speak. With this production method, a glycolide can be produced efficiently by the following reasons.

(1) By inducing the depolymerization of the PGA (A) using a uniform solution phase with the polyethylene glycol ether (B) serving as a solvent, the surface area is expanded dramatically, and the production rate of glycolide produced from the surface of the PGA (A) becomes large.

(2) Since the contact between PGAs (A) is suppressed by the diluting effect of the polyethylene glycol ether (B) serving as a solvent, the progression of the polycondensation reaction of a PGA (A) such as a glycolic acid oligomer at the time of heating is suppressed, and the amount of heavy material produced is reduced. Accordingly, the glycolide yield improves, and it is possible to eliminate practically all of the trouble associated with cleaning inside the reactor.

(3) Since the glycolide is produced and distilled off at the distillation temperature of the polyethylene glycol ether (B) serving as a solvent, there is practically no accumulation in the distillation line, so the plugging of the distillation line is prevented, and the trouble of recovering accumulated matter in the distillation line is practically eliminated.

(4) Since a system similar to an ordinary distillation system is used, the scale can be increased easily, and mass production on an industrial scale is also easy.

(5) Further, since the polyethylene glycol ether (B) serving as a solvent for the depolymerization of the PGA (A) undergoes practically no thermal degradation due to depolymerization reaction, the amount of solvent that needs to be newly added can be reduced by once again using the solvent used in the depolymerization reaction for another depolymerization reaction. Accordingly, when mass-producing a glycolide, the solvent cost can be dramatically reduced, and as a result, the glycolide can be mass-produced at low cost.

(6) By using a specific polyethylene glycol ether (B) having a boiling point of from 130 to 220° C. at a pressure of 3 kPa as the solvent for performing the depolymerization of the PGA (A), it is possible to perform the depolymerization reaction of the PGA (A) under milder depolymerization conditions than in conventional techniques, including depolymerization temperature conditions with a temperature of from 200 to 232° C. and preferably from 210 to 230° C. and depolymerization pressure conditions of from 3.6 to 7 kPa and preferably from 4 to 6.8 kPa, for example. As a result, this contributes to energy conservation and makes it possible to suppress the generation of impurities. In addition, there is no decrease in the glycolide production rate, and the loss rate of the PGA serving as a raw material is also small, so glycolide production can be continued over a long period of time.

(7) Similarly, by using the polyethylene glycol ether (B) as a solvent, it is possible to perform the depolymerization reaction of the PGA (A) using a relatively small amount of the solvent with respect to the PGA (A), so the solvent loss is reduced, which also makes it possible to contribute to the conservation of resources.

EXAMPLES

The present invention will be described in further hereinafter using working examples and comparative examples, but the present invention is not limited to these working examples.

The measurement methods for the states or the like of the production steps in the glycolide production method are as follows.

(Glycolide Production Rate)

The GL production rate in the depolymerization reaction system for producing a glycolide by depolymerizing a PGA was determined with the following method. Specifically, the glycolide and solvent that were distilled off in one hour immediately after the PGA depolymerization reaction was begun (initial stage) and in the first one hour after 10 days had passed, after 20 days had passed, and after 30 days had passed, respectively, were used. The mixture was cooled with warm water at a temperature of 85° C. so as to separate the glycolide and the solvent, and the glycolide was recrystallized with ethyl acetate. The mass (g) of the glycolide and the solvent was respectively measured, and the GL production rate (units: g/hour) was determined immediately after the reaction was begun and at points after 10 days had passed, after 20 days had passed, and after 30 days had passed after the depolymerization reaction was begun.

(Diglycolic Acid Concentration in Reaction Solution)

The diglycolic acid concentration in the PGA depolymerization reaction solution was measured by the following method. Specifically, a reaction solution in the reactor was collected immediately after the depolymerization reaction was begun (initial stage) and when 10 days had passed, when 20 days had passed, and when 30 days had passed after the depolymerization reaction was begun, and the diglycolic acid concentration (mass %) in the reaction solution was measured by liquid chromatography.

(Polyglycolic Acid Loss Rate after 10 Days)

The polyglycolic acid loss rate after 10 days (PGA loss rate after 10 days) was calculated (units: mass %) by the following formula based on the ratio of the total of the amount of all glycolide that is distilled off and the amount of polyglycolic acid in the reaction solution (that is, the amount of polyglycolic acid remaining in the reaction solution when the depolymerization reaction was ended) with respect to the amount of all of the polyglycolic acid introduced during the period in which the depolymerization reaction of the polyglycolic acid was continued for 10 days (units: g; same hereafter).

PGA loss rate(mass %)=100−((amount of all distilled glycolide+amount of polyglycolic acid in reaction solution)/amount of all introduced polyglycolic acid)×100    (Formula)

Working Example 1

A mixture (depolymerization composition) consisting of a PGA (A), a solvent (B), and a solubilizing agent (C), was prepared by charging 160 g of a glycolic acid oligomer (weight average molecular weight: 19,000 (measured by GPC; same hereafter)) as a PGA (A) into a 500 ml flask (reactor) to which a cooler was connected, adding 35 g of an ethylene glycol butyl dodecyl ether (boiling point at a pressure of 3 kPa: 211° C.; also called "solvent 1" hereafter) as a polyethylene glycol ether (B) serving as a solvent (also called "solvent (B)" hereafter) (equivalent to 21.9 parts by mass per 100 parts by mass of the PGA (A)), and further adding a solubilizing agent (C) consisting of 89 g of a tetraethylene glycol monooctyl ether as a solubilizing agent (C1) and 35 g of polyethylene glycol dimethyl ether #500 (number average molecular weight: 500, produced by the NOF Corporation) as a solubilizing agent (C2). After a dehydration operation was performed for 1 hour at a temperature of 210° C. by heating the depolymerization composition with a heater (current heating) installed around the flask serving as a reactor in a nitrogen gas atmosphere, the depolymerization composition was heated to a temperature of 225° C. (heating step). It was confirmed visually that the PGA (A) dissolved uniformly in the solvent and that a solution state with essentially no phase separation was formed (solution-forming step).

When the pressure inside the flask was reduced to 4.1 kPa while continuing to heat the mixture in a solution state at a temperature of 225° C., the production of a glycolide began with the depolymerization reaction of the PGA (A) (glycolide production step), and the codistillation of the glycolide and the solvent (B) began. The heating current was adjusted so as to maintain a temperature of 225° C., and heating was continued under reduced pressure (distillation step). The distilled glycolide and the solvent (B) were cooled by the cooler and recovered each time one hour passed (recovery step). The PGA (A) and the solvent (B) were additionally introduced into the reactor in an amount corresponding to the measured amount of the distilled glycolide, and the depolymerization reaction was continued for 30 days. The results of measuring the amount of glycolide (g/hour) collected (GL production rate (g/hour)) immediately after the reaction was begun (initial stage) and at points after 10 days had passed, after 20 days had passed, and after 30 days had passed after the reaction was begun, the diglycolic acid concentration (mass %) (also called the "DGA concentration) (mass %) in the reaction solution" hereafter), and the PGA loss rate (mass %) after 10 days had passed after the reaction was begun are shown in Table 2.

Working Example 2

A glycolide was produced by depolymerizing a PGA (A) in the same manner as in Working Example 1 with the exception that the heating conditions in the glycolide production step were changed to a temperature of 230° C. and a pressure of 4.7 kPa. The results of measuring the GL production rate (g/hour), the DGA concentration (mass %) in the reaction solution, and the PGA loss rate after 10 days had passed are shown in Table 2.

Working Example 3

A glycolide was produced by depolymerizing a PGA (A) in the same manner as in Working Example 1 with the exception that 70 g of solvent 1 serving as the solvent (B) was used, the solubilizing agent (C2) was not used, and the heating conditions in the glycolide production step were changed to a temperature of 225° C. and a pressure of 5.0 kPa. The results of measuring the GL production rate (g/hour), the DGA concentration (mass %) in the reaction solution, and the PGA loss rate after 10 days had passed are shown in Table 2.

Working Example 4

A glycolide was produced by depolymerizing a PGA (A) in the same manner as in Working Example 1 with the exception that an ethylene glycol dioctyl ether (boiling point at a pressure of 3 kPa: 195° C.; also called "solvent 2" hereafter) was used as the solvent (B), and the temperature and pressure in the glycolide production step were changed to a temperature of 220° C. and a pressure of 4.5 kPa. The results of measuring the GL production rate (g/hour), the DGA concentration (mass %) in the reaction solution, and the PGA loss rate (mass %) after 10 days had passed are shown in Table 2.

Working Example 5

A glycolide was produced by depolymerizing a PGA (A) in the same manner as in Working Example 4 with the exception that the temperature and pressure in the glycolide production step were changed to a temperature of 230° C. and a pressure of 6.8 kPa. The results of measuring the GL production rate (g/hour), the DGA concentration (mass %) in the reaction solution, and the PGA loss rate (mass %) after 10 days had passed are shown in Table 2.

Working Example 6

A glycolide was produced by depolymerizing a PGA (A) in the same manner as in Working Example 4 with the exception that 70 g of solvent 2 serving as the solvent (B) was used, the solubilizing agent (C2) was not used, and the heating conditions in the glycolide production step were changed to a temperature of 220° C. and a pressure of 5.5 kPa. The results of measuring the GL production rate (g/hour), the DGA concentration (mass %) in the reaction solution, and the PGA loss rate (mass %) after 10 days had passed are shown in Table 2.

Comparative Example 1

A glycolide was produced by depolymerizing a PGA (A) in the same manner as in Working Example 1 with the exception that 70 g of a triethylene glycol butyl octyl ether (boiling point at a pressure of 3 kPa: 223° C.; does not belong to the category of the solvent (B) used in the present invention; also called "solvent 3" hereafter) was used as a solvent instead of solvent 1 serving as the solvent (B) (equivalent to 43.8 parts by mass per 100 parts by mass of the PGA), the solubilizing agent (C2) was not used, and the heating conditions in the glycolide production step were changed to a temperature of 230° C. and a pressure of 2.8 kPa. The results of measuring the GL production rate (g/hour), the DGA concentration (mass %) in the reaction solution, and the PGA loss rate (mass %) after 10 days had passed are shown in Table 2.

Comparative Example 2

When a glycolide was produced by depolymerizing a PGA (A) in the same manner as in Comparative Example 1 with the exception that the heating conditions in the glycolide production step were changed to a temperature of 235° C. and a pressure of 3.3 kPa, the glycolide production stopped before 30 days had passed. The results of measuring the GL production rate (g/hour), the DGA concentration (mass %) in the reaction solution, and the PGA loss rate (mass %) after 10 days had passed are shown in Table 2.

Comparative Example 3

A depolymerization composition (not containing a solubilizing agent) consisting of a PGA and a solvent (solvent 3) was prepared in the same manner as in Comparative Example 1 with the exception that the solubilizing agent (C) was not added and 159 g of solvent 3 was used as a solvent. The depolymerization composition was heated in a nitrogen gas atmosphere, and when a dehydration operation was performed for 1 hour at a temperature of 210° C. and the depolymerization composition was heated to a temperature of 225° C., it was confirmed visually that the PGA (A) was not in a solution state in which the PGA (A) had dissolved uniformly in the solvent.

Heating was continued further, and when the temperature was increased to 235° C. and the pressure inside the flask serving as a reactor was reduced to 3.9 kPa, the distillation of solvent 3 was observed, but codistillation with the glycolide was not observed. The results of measuring the GL production rate (g/hour), the DGA concentration (mass %) in the reaction solution, and the PGA loss rate (mass %) after 10 days had passed are shown in Table 2.

TABLE 2

|  |  | Working Example 1 | Working Example 2 | Working Example 3 |
|---|---|---|---|---|
| Solvent | Type |  | Solvent 1 |  |
|  | Boiling point at 3 kPa pressure |  | 211 |  |
|  | Mass (g) | 35 | 35 | 70 |
| Solubilizing agent | Type | Solubilizing agent (C1) | Solubilizing agent (C1) | Solubilizing agent (C1) |
|  | Mass (g) | 89 | 89 | 89 |
|  | Type | Solubilizing agent (C2) | Solubilizing agent (C2) | — |
|  | Mass (g) | 35 | 35 | — |

TABLE 2-continued

|  |  | | | |
|---|---|---|---|---|
| Heating step | Temperature (° C.) | 225 | 225 | 225 |
|  | Pressure (kPa) | Normal Pressure | Normal Pressure | Normal Pressure |
| Glycolide production step | Temperature (° C.) | 225 | 230 | 225 |
|  | Pressure (kPa) | 4.1 | 4.7 | 5.0 |
| GL production rate (g/hour) | Initial stage | 21.9 | 23.0 | 21.3 |
|  | After 10 days | 17.6 | 17.0 | 17.1 |
|  | After 20 days | 13.3 | 11.0 | 12.9 |
|  | After 30 days | 9.0 | 5.0 | 8.7 |
| DGA concentration in reaction solution (mass %) | Initial stage | 0.0 | 0.0 | 0.0 |
|  | After 10 days | 1.0 | 1.4 | 1.0 |
|  | After 20 days | 2.1 | 2.7 | 2.1 |
|  | After 30 days | 3.1 | 4.1 | 3.1 |
| PGA loss rate (mass %) after 10 days |  | 11.7 | 16.1 | 11.7 |

|  |  | Working Example 4 | Working Example 5 | Working Example 6 |
|---|---|---|---|---|
| Solvent | Type |  | Solvent 2 |  |
|  | Boiling point at 3 kPa pressure |  | 195 |  |
|  | Mass (g) | 35 | 35 | 70 |
| Solubilizing agent | Type | Solubilizing agent (C1) | Solubilizing agent (C1) | Solubilizing agent (C1) |
|  | Mass (g) | 89 | 89 | 89 |
|  | Type | Solubilizing agent (C2) | Solubilizing agent (C2) | — |
|  | Mass (g) | 35 | 35 | — |
| Heating step | Temperature (° C.) | 225 | 225 | 225 |
|  | Pressure (kPa) | Normal Pressure | Normal Pressure | Normal Pressure |
| Glycolide production step | Temperature (° C.) | 220 | 230 | 220 |
|  | Pressure (kPa) | 4.5 | 6.8 | 5.5 |
| GL production rate (g/hour) | Initial stage | 15.3 | 18.0 | 14.9 |
|  | After 10 days | 13.0 | 13.3 | 12.7 |
|  | After 20 days | 10.8 | 8.6 | 10.5 |
|  | After 30 days | 8.5 | 3.9 | 8.3 |
| DGA concentration in reaction solution (mass %) | Initial stage | 0.0 | 0.0 | 0.0 |
|  | After 10 days | 0.8 | 1.4 | 0.8 |
|  | After 20 days | 1.6 | 2.7 | 1.6 |
|  | After 30 days | 2.3 | 4.1 | 2.3 |
| PGA loss rate (mass %) after 10 days |  | 7.4 | 16.1 | 7.4 |

|  |  | Comparative Example 1 | Comparative Example 2 | Comparative Example 3 |
|---|---|---|---|---|
| Solvent | Type |  | Solvent 3 |  |
|  | Boiling point at 3 kPa pressure |  | 223 |  |
|  | Mass (g) | 70 | 70 | 159 |
| Solubilizing agent | Type | Solubilizing agent (C1) | Solubilizing agent (C1) | — |
|  | Mass (g) | 89 | 89 | — |
|  | Type | — | — | — |
|  | Mass (g) | — | — | — |
| Heating step | Temperature (° C.) | 225 | 225 | 225 |
|  | Pressure (kPa) | Normal Pressure | Normal Pressure | Normal Pressure |
| Glycolide production step | Temperature (° C.) | 230 | 235 | 235 |
|  | Pressure (kPa) | 2.8 | 3.3 | 3.9 |
| GL production rate (g/hour) | Initial stage | 30.5 | 30.6 | No distillation |
|  | After 10 days | 22.6 | 20.1 | No distillation |
|  | After 20 days | 14.6 | 9.5 | No distillation |
|  | After 30 days | 6.7 | No distillation | No distillation |
| DGA concentration in reaction solution (mass %) | Initial stage | 0.0 | 0.0 | — |
|  | After 10 days | 1.4 | 1.8 | — |
|  | After 20 days | 2.7 | 3.6 | — |
|  | After 30 days | 4.1 | 5.4 | — |
| PGA loss rate (mass %) after 10 days |  | 16.1 | 20.4 | 20.4 |

It can be seen from Table 2 that in the methods of Working Examples 1 to 6 for producing a glycolide by depolymerizing a PGA comprising:
(I) a heating step of heating a mixture either under normal pressure or reduced pressure at a temperature at which a PGA (A) undergoes depolymerization, the mixture containing the PGA (A) and a polyethylene glycol ether (B) which is represented by the following formula (1):

(wherein X and Y are each independently an alkyl group or an aryl group having from 2 to 20 carbon atoms, and p is an integer from 1 to 5)
and which has a molecular weight of from 150 to 450 and a boiling point of from 130 to 220° C. at a pressure of 3 kPa; (II) a solution-forming step in which the mixture is rendered in a solution state in which a melt phase of the PGA (A) and a liquid phase consisting of the polyethylene glycol ether (B) essentially form a uniform phase; (III) a glycolide production step in which a glycolide is produced by a depolymerization reaction of the PGA (A) by continuing to heat the mixture in the solution state; (IV) a distillation step of distilling off the produced glycolide together with the polyethylene glycol ether (B) from the depolymerization reaction system; and (V) a recovery step of recovering the glycolide from the distillate, there is the merit that glycolide production can be continued over a long period of time due to the following characteristics:
1) glycolide can be produced by a depolymerization reaction of the PGA (A) under relatively mild conditions with a temperature of from 220 to 230° C. and a pressure of from 4.1 to 6.8 kPa;
2) the decrease in GL production rate over time is slow;
3) the production of diglycolic acid as an impurity can be suppressed; and
4) the PGA loss rate after 10 days is at most 16.1 mass %.

In particular, in Working Examples 1, 2, 4, and 5 in which the solubilizing agent (C) contains (C1) a monohydric, dihydric, or higher polyhydric alcohol having a boiling point of 180° C. or higher at normal pressure, and (C2) a non-basic compound (excluding monohydric, dihydric, or higher polyhydric alcohols) having a boiling point of 180° C. or higher at normal pressure and having compatibility with the polyethylene glycol ether (B), the depolymerization reaction of the PGA (A) can be performed by using 21.9 parts by mass of the solvent (B) per 100 parts by mass of the PGA (A), and it was thus determined that there is an effect of reducing the amount of the solvent (B) that is used to perform the depolymerization reaction of the PGA (A).

In contrast, in the methods for producing a glycolide according to Comparative Examples 1 and 2, in which a solvent 3 in the form of a polyethylene glycol ether having a boiling point that is not within the range of from 130 to 220° C. at a pressure of 3 kPa is used as a solvent, it is not possible to produce a glycolide by a depolymerization reaction of the PGA (A) without using stringent conditions with a temperature of 235° C. or a pressure of 2.8 kPa, even if the amount of solvent that is used is set to 43.8 parts by mass per 100 parts by mass of the PGA (A), and the increase in the amount of DGA produced as an impurity associated with the continuation of the depolymerization reaction of the PGA (A) is marked. In addition, the depolymerization conditions involve a high temperature and/or a low pressure, and it was thus determined that although the initial glycolide production rate is large, the decrease in the glycolide production rate over time is rapid, so the depolymerization reaction of the PGA ends in a short period of time. In addition, when solvent 3 is used and when a solubilizing agent is not used in Comparative Example 3 and subsequent comparative examples, it is clear that it is not possible to produce a glycolide by a depolymerization reaction of the PGA (A), even if the amount of the solvent that is used is set to a very high level of 99.4 parts by mass per 100 parts by mass of the PGA (A) and stringent depolymerization conditions with a temperature of 235° C. are used.

INDUSTRIAL APPLICABILITY

The present invention is
a method for producing a glycolide by depolymerizing a polyglycolic acid, the method comprising:
(I) a heating step of heating a mixture either under normal pressure or reduced pressure at a temperature at which a polyglycolic acid (A) undergoes depolymerization, the mixture containing the polyglycolic acid (A) and a polyethylene glycol ether (B) which is represented by the following formula (1):

(wherein X and Y are each independently an alkyl group or an aryl group having from 2 to 20 carbon atoms, and p is an integer from 1 to 5)
and which has a molecular weight of from 150 to 450 and a boiling point of from 130 to 220° C. at a pressure of 3 kPa;
(II) a solution-forming step in which the mixture is rendered in a solution state in which a melt phase of the polyglycolic acid (A) and a liquid phase consisting of the polyethylene glycol ether (B) essentially form a uniform phase;
(III) a glycolide production step in which a glycolide is produced by a depolymerization reaction of the polyglycolic acid (A) by continuing to heat the mixture in the solution state;
(IV) a distillation step of distilling off the produced glycolide together with the polyethylene glycol ether (B) from the depolymerization reaction system; and
(V) a recovery step of recovering the glycolide from the distillate.

As a result, a method capable of continuing a reaction for a long period of time without any decrease in production efficiency and efficiently and economically producing a glycolide by depolymerizing a polyglycolic acid is provided, which yields high industrial applicability.

The invention claimed is:
1. A method for producing a glycolide by depolymerizing a polyglycolic acid, the method comprising:
(I) a heating step of heating a mixture either under normal pressure or reduced pressure to depolymerize a polyglycolic acid (A) wherein a range for the temperature at which the polyglycolic acid (A) undergoes depolymerization is from 190° C. to 232° C., the mixture containing the polyglycolic acid (A) and a polyethylene glycol ether (B) which is represented by the following formula (1):

wherein X and Y are each independently an alkyl group or an aryl group having from 2 to 20 carbon atoms, and p is 1;
and which has a molecular weight of from 150 to 450 and a boiling point of from 130 to 220° C. at a pressure of 3 kPa;
(II) a solution-forming step in which the mixture is rendered in a solution state in which a melt phase of the polyglycolic acid (A) and a liquid phase consisting of the polyethylene glycol ether (B) form a substantially uniform phase;

(III) a glycolide production step in which a glycolide is produced by a depolymerization reaction of the polyglycolic acid (A) by continuing to heat the mixture in the solution state under reduced pressure of from 3 to 90 kPa;

(IV) a distillation step of distilling off the produced glycolide together with the polyethylene glycol ether (B) from the depolymerization reaction system; and (V) a recovery step of recovering the glycolide from the distillate.

2. The method for producing a glycolide according to claim 1, wherein the polyethylene glycol ether (B) is a polyethylene glycol ether in which a glycolide solubility at a temperature of 85° C. is from 0.1 to 5 mass %.

3. The method for producing a glycolide according to claim 1, wherein the polyethylene glycol ether (B) is a polyethylene glycol ether in which both X and Y in the formula (1) are alkyl groups, and a total of the number of carbon atoms of these alkyl groups is from 5 to 28.

4. The method for producing a glycolide according to claim 1, wherein in step (I), the polyethylene glycol ether (B) is mixed at a ratio of from 10 to 100 parts by mass per 100 parts by mass of the polyglycolic acid (A).

5. The method for producing a glycolide according to claim 1, wherein in steps (I) to (III), the mixture is heated to a temperature of from 200 to 232° C.

6. The method for producing a glycolide according to claim wherein in steps (I) to (III), the mixture further contains a solubilizing agent (C).

7. The method for producing a glycolide according to claim 6, wherein the solubilizing agent (C) is a non-basic compound having a boiling point of 180° C. or higher at normal pressure.

8. The method for producing a glycolide according to claim 6, wherein the solubilizing agent (C) is at least one type selected from the group consisting of monohydric, dihydric, or higher polyhydric alcohols, phenols, monohydric, dihydric, or higher polyhydric aliphatic carboxylic acids, aliphatic amides of aliphatic carboxylic acids and amines, aliphatic imides, and polyalkylene glycol ethers having a molecular weight greater than 450.

9. The method for producing a glycolide according to claim 6, wherein the solubilizing agent (C) contains a polyalkylene glycol represented by formula (2):

$$HO\text{—}(\text{—}R^1\text{—}O\text{—})_q\text{—}H \qquad (2)$$

wherein $R^1$ is a methylene group or a straight-chain or branched alkylene group having from 2 to 8 carbon atoms, q is an integer of 1 or greater, and when q is 2 or greater, a plurality of $R^1$ moieties may be the same or different from one another.

10. The method for producing a glycolide according to claim 9, wherein the polyalkylene glycol is at least one type selected from the group consisting of polyethylene glycols, polypropylene glycols, and polybutylene glycols.

11. The method for producing a glycolide according to claim 6, wherein the solubilizing agent (C) contains a polyalkylene glycol monoether represented by formula (3):

$$HO\text{—}(\text{—}R^2\text{—}O\text{—})_r\text{—}X^1 \qquad (3)$$

wherein $R^2$ is a methylene group or a straight-chain or branched alkylene group having from 2 to 8 carbon atoms, $X^1$ is a hydrocarbon group, r is an integer of 1 or greater, and when r is 2 or greater, a plurality of $R^2$ moieties may be the same or different from one another.

12. The method for producing a glycolide according to claim 11, wherein the polyalkylene glycol monoether is at least one type selected from the group consisting of polyethylene glycol monoethers, polypropylene glycol monoethers, and polybutylene glycol monoethers.

13. The method for producing a glycolide according to claim 11, wherein the polyalkylene glycol monoether has an alkyl group having from 1 to 18 carbon atoms as an ether group thereof.

14. The method for producing a glycolide according to claim 6, wherein the solubilizing agent (C) contains (C1) a monohydric, dihydric, or higher polyhydric alcohol having a boiling point of 180° C. or higher at normal pressure, and (C2) a non-basic compound excluding monohydric, dihydric, or higher polyhydric alcohols having a boiling point of 180° C. or higher at normal pressure.

15. The method for producing a glycolide according to claim 6, wherein the solubilizing agent (C) is added at a ratio of from 0.1 to 500 parts by mass per 100 parts by mass of the polyglycolic acid (A).

16. The method for producing a glycolide according to claim 1, wherein in step (V), the distillate is cooled with a condenser, the glycolide and the polyethylene glycol ether (B) are phase-separated in a liquid state, and the glycolide phase is separated and recovered.

17. The method for producing a glycolide according to claim 16, wherein the distillate is cooled at a temperature of from 85 to 180° C., and the glycolide and the polyethylene glycol ether (B) are phase-separated in a liquid state.

18. The method for producing a glycolide according to claim 16, wherein phase separation is performed while continuing the depolymerization reaction, and the glycolide in the distillate is condensed in the glycolide phase of the lower layer.

19. The method for producing a glycolide according to claim 16, wherein the polyethylene glycol ether (B) phase is separated and circulated to the depolymerization reaction system.

20. The method for producing a glycolide according to claim 1, wherein the polyethylene glycol ether (B) has a boiling point of from 230 to 450° C. at normal pressure.

* * * * *